(12) United States Patent
Toimela

(10) Patent No.: US 9,408,580 B2
(45) Date of Patent: Aug. 9, 2016

(54) APPARATUS AND METHOD FOR GENERATING DENTAL PANORAMIC IMAGES

(71) Applicant: Planmeca Oy, Helsinki (FI)

(72) Inventor: Lasse Toimela, Espoo (FI)

(73) Assignee: Planmeca Oy, Helsinki (FI)

( * ) Notice: Subject to any disclaimer, the term of this patent is extended or adjusted under 35 U.S.C. 154(b) by 215 days.

(21) Appl. No.: 14/133,617

(22) Filed: Dec. 18, 2013

(65) Prior Publication Data

US 2015/0164446 A1    Jun. 18, 2015

(51) Int. Cl.
*A61B 6/14* (2006.01)
*G06T 3/40* (2006.01)
*A61B 6/04* (2006.01)
*A61B 6/00* (2006.01)

(52) U.S. Cl.
CPC .............. *A61B 6/14* (2013.01); *A61B 6/5241* (2013.01); *A61B 6/547* (2013.01); *G06T 3/4038* (2013.01); *A61B 6/04* (2013.01); *A61B 6/4435* (2013.01)

(58) Field of Classification Search
CPC .... A61B 6/14; G06T 3/4038; G06T 2200/32; G06T 2210/41
USPC .......................... 378/38–40, 62, 98.11, 98.12
See application file for complete search history.

(56) References Cited

U.S. PATENT DOCUMENTS

| 2006/0274881 A1* | 12/2006 | Singh | A61B 6/14 378/38 |
| 2008/0063139 A1* | 3/2008 | Pantsar | A61B 6/14 378/40 |

* cited by examiner

*Primary Examiner* — Courtney Thomas
(74) *Attorney, Agent, or Firm* — Brundidge & Stanger, P.C.

(57) ABSTRACT

The invention generally relates to generating digital dental panoramic images from multiple frame images acquired during a dental panoramic imaging scan about a patient's head. This generating includes using information of location and orientation of the x-ray beam and the x-ray detector at times when taking the frames in the procedure of summing information of the frames.

22 Claims, 6 Drawing Sheets

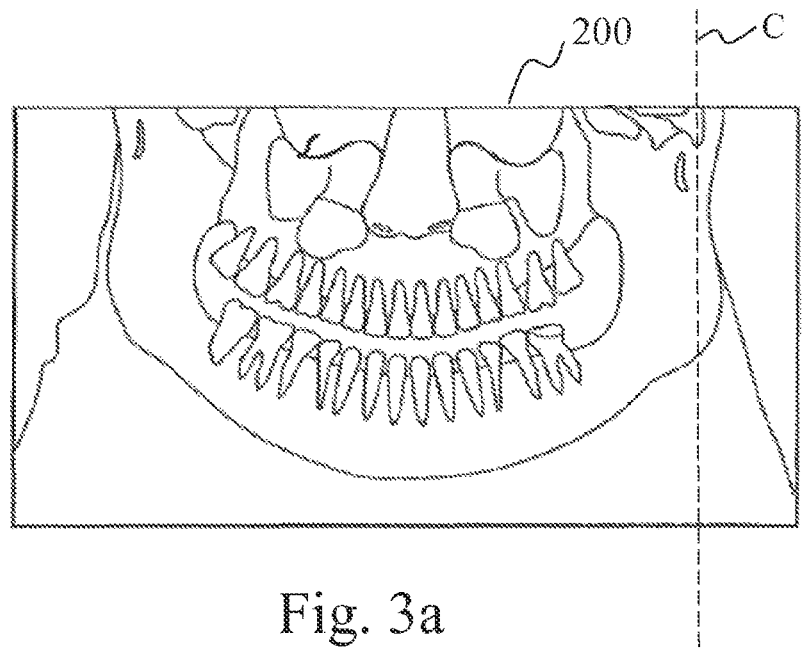
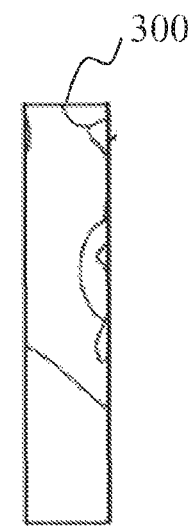
Fig. 3a  Fig. 3b
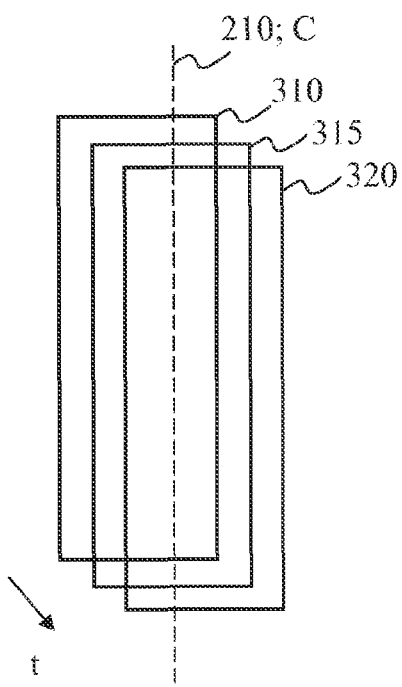
Fig. 4

APPARATUS AND METHOD FOR GENERATING DENTAL PANORAMIC IMAGES

TECHNICAL FIELD

The invention generally relates to dental panoramic imaging and, more particularly, to generating digital dental panoramic images from multiple frame images acquired during a dental panoramic imaging scan about a patient's head.

BACKGROUND OF INVENTION

A traditional operation principle of panoramic X-ray apparatuses includes driving an X-ray source and a film cassette around a patient's head while a film is moved with respect to the X-ray beam in such a way that the dental arch will be imaged as a planar picture on the film.

This basic operation of the traditional dental panoramic imaging includes creating a respective mutual movement between the X-ray source, the image information receiver and the patient.

While there are number of possibilities to create such movement, the most common arrangement has been to attach the X-ray source and the image information receiver to a support arm at a distance from each other, which arm is then moved in a specific way with respect to a stationary patient. In such context, in order to obtain a sharp image of a desired layer within the object, i.e. the layer of a dental arch within a patient's head, the velocity of movement of the film has to be specifically correlated with the sweep velocity of the X-ray beam along the desired layer to be imaged. By this arrangement, the undesirable structures in front of and behind the desired layer within the patient's head are blurred invisible.

In the traditional panoramic imaging, the thickness of the layer that will be photographed sharp is directly proportional to the distance of the instantaneous center of rotation of the support arm from the film level, and inversely proportional to the magnification and to the width of the beam.

This basic equation of panoramic imaging can be expressed as follows:

$$v1/v0 = L1/L0$$

$$v0 = \omega r$$

where:
L0=distance from the X-ray tube focus F to a point of the object being imaged at a given moment;
L1=distance from the X-ray tube focus F to the X-ray film (or detector) plane;
ω=angular velocity of rotational movement about the instantaneous center of rotation;
r=distance of the point of the object being imaged from the instantaneous center of rotation; and
v1=velocity of the image point on the film (detector) plane.

The velocity v1 thus relates to the speed by which the film is moved during the panoramic imaging scan relative to the x-ray beam hitting the film. As to digital imaging, when a so-called TDI imaging technique (Time Delayed Integration) is used, the transfer velocity of pixel charges across the detector is made to correspond to the velocity of film movement. Thus, the image data read out from the sensor will correspond to the panoramic film image in the sense that blurring of the layers outside the desired layer is already done when the scanning process and charge transfer are carried out so as to follow this imaging equation. In this context, as far as selecting the tomographic layer to be shown is concerned, post exposure image processing is not needed nor would it even be possible, as the data read out from the sensor already represents the very layer the velocity v1 corresponds to.

Prior art digital panoramic imaging also includes a so-called FT (Frame Transfer) technique. When using FT or any other technique in which a number of individual overlapping frames are shot during the imaging scan, when one wishes to view the same layer as one would get when following the traditional panoramic imaging equation presented above, the degree of overlap of the frames when constructing the layer to be viewed as sharp shall be made to correspond to the velocity v1.

One advantage the frame technique brings along is that since the degree of overlap of the frames used in the image processing determines the layer that will be relatively intensified while the others will be blurred, by altering the degree of overlap on can change the tomographic layer to a certain degree after the exposure. The extent one is able to alter the layer depends on how and by which kind of means the frame data has been acquired. Typically, however, only marginal changes in the location of the layer are possible.

Still, while the prior art frame panoramic systems include the possibility to marginally alter the sharp layer, the degree of overlap used in the image construction is based on some predetermined scheme. These schemes typically include using a standard overlap of the frames and the actual calculation of the panoramic image does not include any parameter which would relate to the actual imaging geometry of the imaging system at the exposure positions of the frames.

Further, as the viewing direction of the anatomy is primarily dictated by the imaging geometry used to obtain the frame data, i.e. by the geometry according to which the imaging means (the x-ray source and the image information receiver) move when the frame data is acquired, the prior art systems are stuck with that viewing direction as they lack means to alter a viewing direction from which the panoramic images or sections of them are shown.

Further, even though the frame imaging technique makes it possible to use wider detector areas than possible in practice when using the more traditional continuous scanning techniques, there are criteria such as those relating to the necessity to be able to read out a frame fast enough during the imaging scan, as well as not to have major alterations in the magnification ratio within a single frame, which have set practical limits also to the width of the detectors one can use in the prior art dental panoramic frame imaging.

SUMMARY OF THE INVENTION

The main objective of the invention and its preferable embodiments is to provide a system by which the frame image data acquired in a single panoramic imaging scan can be used in relation to knowledge of the true imaging geometry used in the imaging procedure, regarding each exposure position, so as to provide new possibilities for generating dental panoramic images from the frame data after the exposure. Secondary objectives of the invention include making it possible to not only generate more than one tomogaphic layer from the frame image data acquired in a single panoramic imaging scan but also to construct and display images or partial images of dental arch as viewed from different directions.

These and other objectives of the invention that will be discussed below can be reached by embodiments of the invention as defined in the attached claims. The core of the invention is to implement the panoramic scan so that information of the imaging geometry, that is location and orientation of the detector and of the focus of the x-ray tube and, and thus of the x-ray beam, is known at their exposure positions and this information is then used in calculating a dental panoramic image.

Advantages the various embodiments of the invention provide includes a possibility to be able to generate dental panoramic images from a single frame data set as viewed from more than one direction. When it is possible to virtually change the viewing angle, features of an anatomy may become visible which are not visible from a particular other viewing direction. Thus, e.g. re-exposure of a patient to x-radiation due to a need for a re-take of the image may be avoided. Further, embodiments discussed below provide a possibility to use wider detectors than typically used in dental frame panoramic imaging.

BRIEF DESCRIPTION OF THE DRAWINGS

The invention and some of its preferable embodiments will be discussed below, by also referring to the attached Figs, out of which FIG. 3a shows a dental panoramic image and FIG. 3b an individual frame image out of number of which a dental panoramic image may be generated, FIG. 4 shows individual overlapping frames together with a line representing a vertical section of an anatomy which is projected at different locations of the frames as an imaging detector is moved to new exposure positions.

DETAILED DESCRIPTION OF INVENTION

The embodiments discussed herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

It should also be understood that the embodiments are exemplary. For example, in case the specification refers somewhere to "an", "one", or "some" embodiment(s), this does not necessarily mean that each such reference is to the same embodiment(s), or that the feature only applies to a single embodiment. Single features of different embodiments may be combined to provide other embodiments, even if that has not been explicitly disclosed in a given context.

The embodiments of the invention discussed herein use location and orientation information of an x-ray beam and an x-ray detector when taking overlapping frames along a dental arch to generate a dental panoramic image. For example, embodiments discussed below permit a user to view specific points of interest of the dental arch from an angular area, i.e. from more than one viewing direction. Thus, the embodiments described herein may permit the user to view specific features between a patient's teeth in a dental panoramic radiograph, for example, which features may be invisible in another dental panoramic radiograph generated using prior art methods and arrangements.

Figure 1:
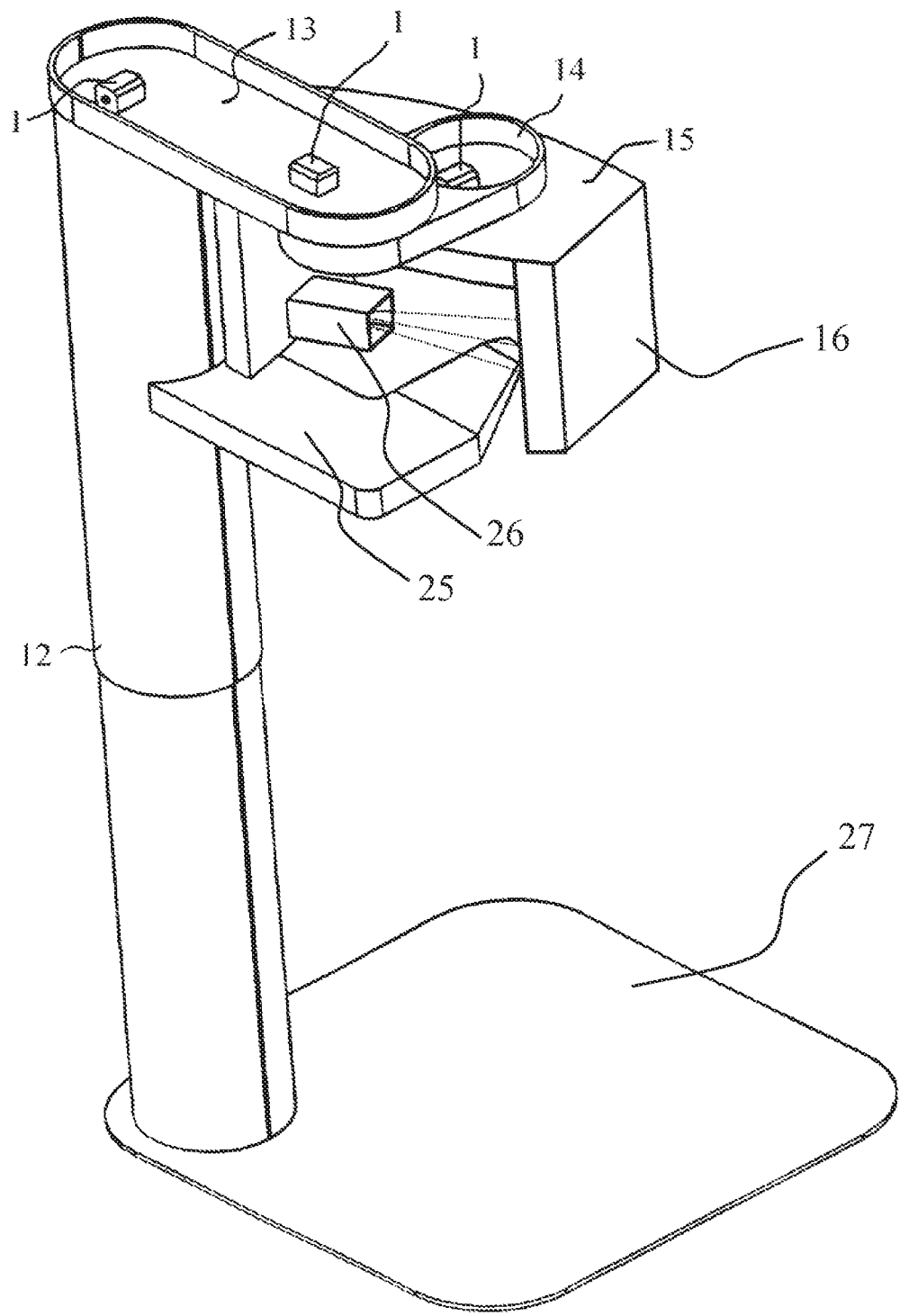
FIG. 1 shows an example of a panoramic imaging apparatus.

Of the attached figures, FIG. 1 presents a structure of an exemplary panoramic X-ray imaging apparatus. The apparatus comprises a base 27 and a column-like frame part 12 fixed by its lower end to the base 27. A supporting arm 13 (shown without its cover) is rotatably mounted on the upper end of the frame part 12. Correspondingly, rotatably mounted on the outer end of the supporting arm 13 is another, intermediate supporting arm 14 on the outer end of which is further rotatably mounted an imaging arm 15, or a C-arm as it is often called. The C-arm 15 supports the imaging means, i.e. an x-ray source 26 and an image detector 16. Moreover, a positioning support 25 is attached to the column-like frame part 12 to help in positioning the person to be imaged. Instead of on the column-like frame part 12, the rotatable supporting arm 13 may as well be mounted on wall or ceiling structures.

The structure illustrated in FIG. 1 has been simplified for the sake of clarity. For example, force receiving means serving as transmission means of the arm structures 13-15 are not shown in the figure. Likewise, the stepping motors 1 to rotate the arm structures 13-15 are depicted in a simplified form.

The apparatus as shown in FIG. 1 and its control system (not shown in FIG. 1) provides an example of a structure for moving the rotation centre of the C-arm 15 which carries the imaging means to perform a panoramic imaging scan about a patients head using basically any shape of trajectory of the rotation centre one desires. Structures of dental panoramic imaging apparatus vary and at the simplest, the imaging apparatus may allow for just one fixed imaging geometry.

Figure 2:
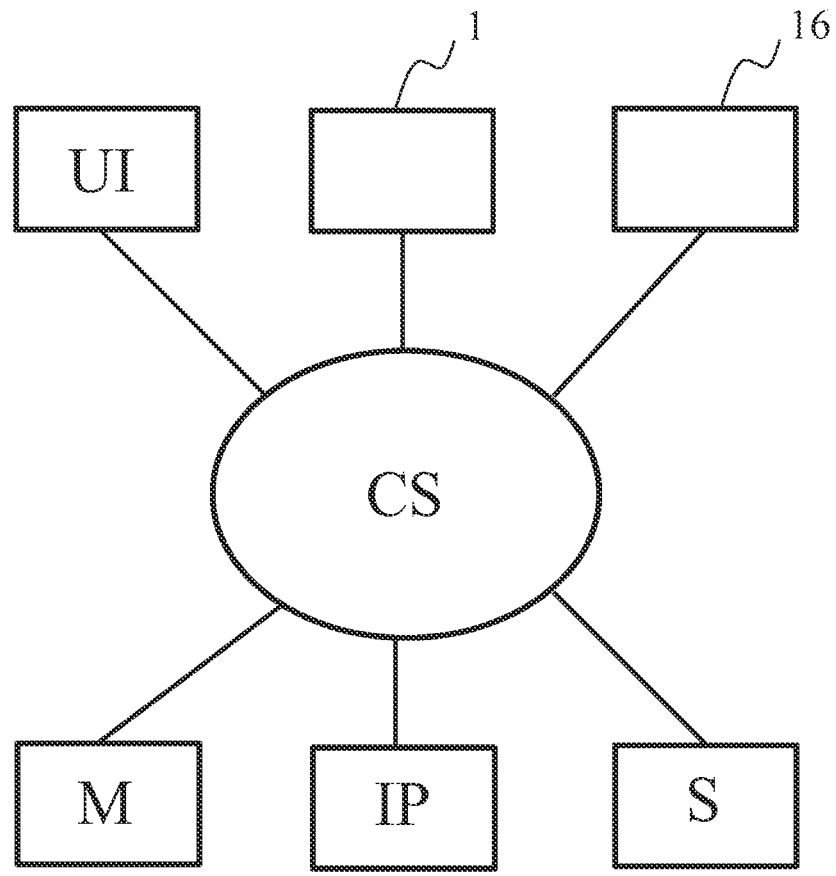
FIG. 2 shows some of the basic components of a system to implement the embodiments discussed below.

The basic components of a system to implement the invention, as shown in FIG. 2, include a control system CS of the imaging apparatus, which includes or is in operational connection with motors 1 that drive the arm or the arms 13-15 of the apparatus, and with operating electronics of the detector 16. The system includes a memory M for, amongst other, recording frame image information and information regarding the related imaging geometry, processing means IP to create a panoramic image, a screen S on which to show images and a user interface UI.

FIG. 3A shows a typical dental panoramic image 200. When a digital panoramic image 200 is constructed from frame image data acquired during a panoramic imaging scan, FIG. 3B can be considered representing one of hundreds or thousands of partially overlapping frame images 300 that are taken during the scan. FIG. 4 then shows a principle of how overlapping individual frames 310, 315, 320 acquired during a panoramic imaging scan can be used in constructing the digital panoramic image 200. Line 210 which vertically spans the frames 310, 315, 320 represents location of a pixel column in each of the frames which includes image information of the same thin vertical section of the anatomy being imaged. The image information these columns include is used to construct a pixel column C of the final digital panoramic image 200 to be generated, as to be discussed in more detail below. Frames taken before frame 310 and after frame 320 which do not do not intersect the line 210 and thus do not include information concerning the particular section of the anatomy the line 210 represents, will not contribute to that particular column C of the panoramic image 200 being generated.

Figure 5:
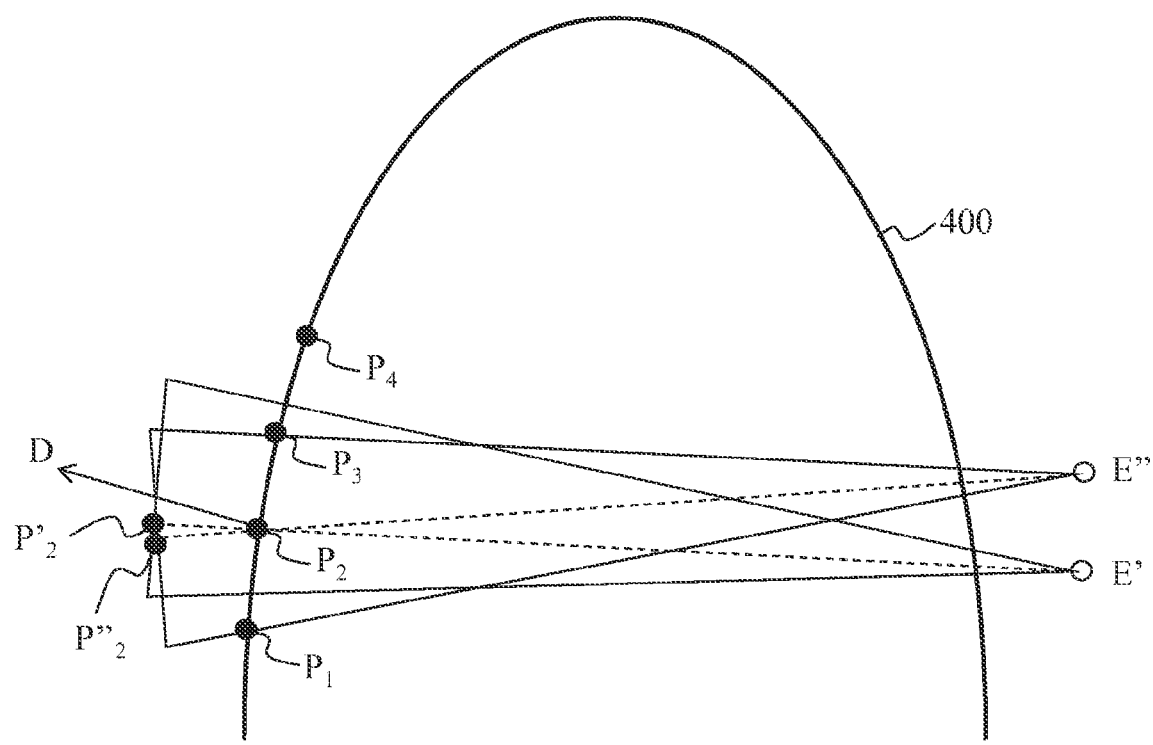
FIG. 5 shows a schematic drawing of the principle of the panoramic imaging process according to an embodiment of the invention.

FIG. 5 shows a schematic drawing to explain principles of the panoramic imaging process of the invention. The process uses what will be called here a virtual panoramic curve 400, together with data of location of and orientation of the imaging means during exposure in the coordinate system of this curve.

To put this in other words and as will be discussed in further detail below, the process includes placing a virtual panoramic curve 400 which represents location and shape of the tomographic layer to be generated in the coordinate system of the imaging geometry used when shooting the frame data.

In FIG. 5, a number of points (P1, P2, P3, P4) are shown on the panoramic curve 400, each of which can be considered corresponding to a location of a section of anatomy to be shown in the panoramic image. In other words, each point (P1, P2, etc.) represents location of a vertical layer of a dental arch which is to be shown as an individual pixel column in the generated digital panoramic image.

FIG. 5 further shows two exposure positions, i.e. positions (E', E") of the x-ray source and the detector at the time of an exposure and, thus, that of the x-ray beam which penetrates the anatomy being imaged and hits the detector. When this imaging geometry is known, one will be able to determine the location of projection P' of each point P on the detector, at each of the exposure positions in which a projection P' falls on the detector. These projection points P' determine pixel columns on the detector which are to be used in constructing the column C of the panoramic image, which represents a given point PN of the anatomy, which projection P->P' can be considered defining a projection direction of the point P concerning a particular individual frame 300.

As can be seen in FIG. 5, in the first of the exposure positions E' the projection P'2 of point P2 as seen from the focus of the radiation source falls on the detector (a frame) at a location which is quite far from the centre of the detector while in the second position E", the projection P"2 falls basically at the centre of the detector. This is an occurrence a prior art image constructing process might miss in summing columns of overlapping frames by some standard predetermined procedure, while the embodiments discussed here make it possible to select columns to be used in constructing the panoramic image based on actual knowledge of the imaging geometry. In other words, instead of just adding column information of overlapping frames according to some standard summing protocol, one determines that particular column of each of the frame images where a projection of any particular point P1, P2 etc. lies, when viewed from the instantaneous location of the focus of the X-ray beam at the time of shooting the image, and uses specifically those columns in calculating columns C of the panoramic image being generated.

Knowing the imaging geometry, i.e. location and orientation of the X-ray source and the detector during the imaging scan, it also becomes possible by changing the shape or orientation, or both, of the panoramic curve 400 to not only calculate different layers of the anatomy as such but also to construct and display object layers viewed from different directions. This feature of the invention can be understood by considering that the panoramic curve 400 of FIG. 5 would be say slightly turned counter-clockwise about point P4. Considering the imaging positions E' and E", this would bring projections P'2 and P"2 more to the left on the detector (on a frame, as viewed from the direction of the focus of the x-ray source) and thus, different pixel column information would be selected to be used in constructing the panoramic image. These different columns would then represent not only a different layer but also a different angle of view of the object than that according to FIG. 5.

In principle, one can use a virtual panoramic curve 400 of any shape and arranged in any orientation in the coordinate system of the imaging geometry. This allows for constructing tomographic layers having shapes even the very versatile apparatus of FIG. 1 could not create by mere mechanical movements of the arm construction of the apparatus.

As a further aspect, an individual local viewing vector D for any number of points P1, P2 etc. may be determined. In addition to what has been discussed above referring to FIG. 5, a vector D is included in the drawing to denote a desired local viewing direction of point P2. Such vectors D can be used to determine weighting factors for pixel values of the columns of the frames representing particular points P1, P2 etc. of the anatomy. For example, as one can see in FIG. 5, the angle between vector D and the projection direction defined by the line starting from the focus of the radiation source and ending at a projected point P' is somewhat greater in the second E" than in the first exposure position E' of FIG. 5. When this type of embodiment is applied, relatively less weight in the image construction would be given to the pixel values of the column of the projected point P"2 of the second exposure than for values of the projected point P'2 of the first exposure. When this principle is applied to a projection P' of point P, i.e. when more weight is given to pixel values of a certain projection direction than to others, features of the anatomy as view from the favoured direction will become emphasized.

Figure 6:
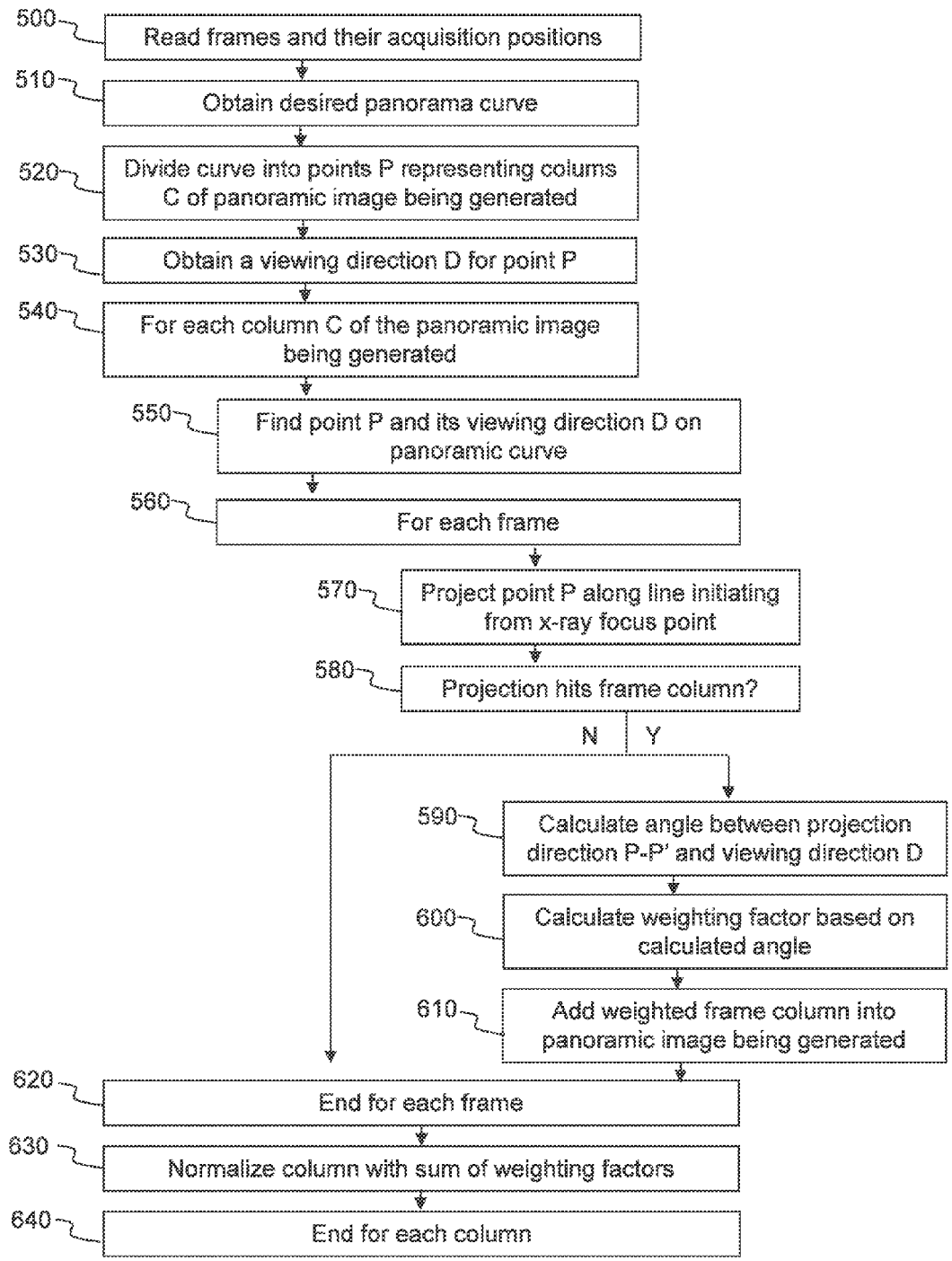
FIG. 6 shows steps of a method in which principles of the invention are applied and FIG. 7 shows a schematic drawing illustrating a hardware configuration of an information handling/computer system which can be used when implementing the invention.

A flow diagram shown in FIG. 6 illustrates one preferred method to implement the principles of the invention. In the first step 500 of the FIG. 7 method, frames and respective exposure positions of the frames during a panoramic imaging scan which has been performed are read. Next, in step 510, the virtual panorama curve one wishes to use in the image construction is obtained, which curve is then divided in step 520 into a plurality of points P—or, in other words, a plurality of points P are selected from the curve, preferably equidistantly, to define points of the anatomy which are to correspond columns C of the panoramic image being generated. An individual viewing direction D for points P may be determined in step 530.

In practice, in view of the imaging geometry to be used in the panoramic imaging scan, it would be preferable that one is aware of the virtual panoramic curve or curves 400 planned to be used in the image construction so that the imaging geometry will reasonable enable generating such desired layer or layers.

Having all the data now available, generating columns C of the panoramic image 200 to be constructed may commence (step 540). First, a point P which corresponds to a column C of the panoramic image, and a related local viewing direction D if such has been determined for a point P is found in step 550. Then, as the panorama curve 400 and respective locations and orientations upon exposure of each frame and of the radiation source are known, a process can be performed for each of the frames (step 560) in which, first, a point P is projected to a frame along a line which originates from the focus of the radiation source in step 570. In practice, concerning most of the frames, there will be no projected point P' as a line originating from the focus of the x-ray source and going through a point P on the panorama curve does not intersect most of the frames but concerning the rest few, the projected point P' on a frame will define the pixel column of that particular frame which is to be used in constructing the column C of the panoramic image the point P in question represents (steps 580 and 610).

In case a local viewing direction D for a given point P has been determined, the process further includes determining the angle between the local viewing direction D and the line originating from the focus of the x-ray source and crossing the point P in question in step 590. This angle can be used as a weighting factor in step 600 to give the less weight in the image construction (step 610) to the frames (i.e. to the pixel values of the projected point P' of the frame) the more the direction of a projection of the point P (or, in other words, in reference to FIG. 5, a vector from P to P') deviates from the desired local viewing direction D. After completion of this process (step 620), the pixel values of each column C of the final panoramic image are normalized by dividing values of a given column by the total sum of the weighting factors of that column.

The procedure discussed above can be presented in more general terms to include using several individual overlapping frames 300 taken along a dental arch by a dental panoramic x-ray imaging apparatus, said apparatus including an x-ray source for generating an x-ray beam and having a focus, and an image detector having pixel columns, the frames 300 being taken by moving the x-ray source and the image detector around a patient's head, and calculating the panoramic image 200 by summing information of the frames 300, and generating the panoramic image 200 by summing information of the frames 300 with respect to information of location and orientation of the x-ray beam and the x-ray detector at times when taking the frames. Summing of information may then include determining location of a desired point or points P with respect to information of location and orientation of the x-ray beam and the x-ray detector at times when taking the frames, whereby the summing of information of the frames 200 then includes summing a column or columns C of the panoramic image 200 with respect to the point or points P. On the other hand, at least two panoramic images 200 as viewed from different directions can be generated and at least two images representing views from different directions then be presented on the display simultaneously, in succession, as a combination image or as a moving image.

An embodiment can also be include generating a virtual panorama curve 400 which represents a tomographic layer to be shown by the panoramic image 200, placing this curve 400 and information of location and orientation of the x-ray beam and the x-ray detector in the same set of coordinates, and generating a panoramic image 200 which represents a tomographic layer according to location of the curve 400 in this set of coordinates.

Yet another embodiment can be include generating a virtual panorama curve 400 with respect to information of location and orientation of the x-ray beam and the x-ray detector which represents a desired tomographic layer to be shown by the panoramic image 200 and, for a column C of the panoramic image 200 being generated, determining the desired point P on the curve 400, and generating a column C of the panoramic image 200 by summing those columns of the individual frames 300 to which the point P as viewed from the focus of the radiation source is projected, this projection P->P' defining a projection direction of the point P concerning the particular individual frame 300.

Concerning the weighting factor, the related process can be presented to include determining a desired viewing direction D for at least one point P whereby a weighting factor is calculated for a column on an individual frame 300 as based on an angle between the viewing direction D and a direction defined by a line from the focus of the radiation source to said point P, the weighting factor then being used when summing information of the frames 300 so as to give the less weight to a column of a frame the greater the angle between said directional vector D representing the desired viewing direction and the direction defined by a line from the focus of the radiation source to the point P.

The virtual panoramic curve used in the embodiment discussed above can be considered to be a tool which makes it possible to alter the tomographic layer in a controlled manner with respect to the imaging geometry used in acquiring the frame data and it can also be used to alter the direction from which the anatomy or a part thereof is viewed. By changing the shape or orientation of the virtual panoramic curve, or both, and even applying the local viewing direction vector discussed above, different images of dental arch can be constructed based on the one and the same set of original x-ray frame image data acquired in a single panoramic imaging scan.

A virtual panorama curve 400 to be used in generating a panoramic image may be defined in a number of different ways. One preferred way is to first generate a curve that fulfils the basic panorama equation discussed above with respect to movements of the imaging means. As movements of the imaging means in a panoramic imaging apparatus of a given type are often fixed, or the same few standard movements are typically used, a panorama curve 400 corresponding to a particular imaging procedure can be created and stored for later use. Additionally, a previously used or stored virtual panorama curve, or a virtual panorama curve just having been used, may be modified e.g. by means which include a linear transformation of all points P and the related viewing directions. The linear transformation may include rotational and translational parts. The modification can also include using a non-linear mapping function such as a two dimensional spline surface, which can be used to deform the panorama curve.

Embodiments of the invention include, as noted, novel ways not only to create dental panoramic images as such but also to show them on a display. For example, when information of location and orientation of the x-ray beam and the x-ray detector at times when taking the frames is available, two or more panoramic images as viewed from different directions can be generated by summing the frame information differently with respect to information of location and orientation of the x-ray beam and the x-ray detector, which in turn makes it possible to display images as viewed from different directions on a display e.g. simultaneously, in succession, as a combination image or as a moving image.

For example, a first and a second virtual panoramic curve with respect to information of location and orientation of the x-ray beam and the x-ray detector can be generated, both of the curves representing a desired layer to be shown by a panoramic image, the second curve being generated from the first one by changing orientation of the first curve, and the two panoramic images then be calculated by summing information of the frames acquired in the panoramic imaging process with respect to these different curves. Of course, more than two curves can be used and e.g. an illusion of turning the dental arch can be generated by showing in succession panoramic images of altering viewing direction. In other words, this type of embodiment may include presenting images on a display in succession according to the order of their viewing direction so as to give an impression of the dental arch turning on the display.

A further embodiment can include generating several panoramic images as viewed from different directions, generating for each such viewing direction several images representing different sharp layers and then, concerning each such viewing direction, one of the several images representing different sharp layers can be selected to represent said viewing direction, after which the images thus selected can be presented on the display—in reference to above, e.g. simultaneously, in succession, as a combination image or as a moving image.

Use of the weighting factor as discussed above may enhance the effect of different viewing angles by emphasizing columns that have a primary x-ray travel path more in line with the viewing angle of the panoramic curve at a given point P.

Using weighting factors also contributes to the possibility to use wider detector surfaces than commonly used in dental frame panorama applications. When the prior art summing of the frame data is based on some standard overlapping procedure, the more likely it becomes that columns that are summed together do not represent the same section of the anatomy the further one goes from the centre of the detector. This is due to the summing protocol not knowing the exact changes in the overall imaging geometry during the exposure process, i.e. the changes there are in mutual positions and orientations of the imaging means and the layer desired to be generated. When using the principles discussed here, though, blurring of the panoramic image due to adding information to the columns C of the panoramic image 200 representing altering locations of the anatomy can be avoided. The weighting factor can also be used to compensate for an altering magnification.

Concerning embodiments of the invention, one possibility to create an illusion of turning an imaged anatomy is to use only one virtual panorama curve yet generate various panoramic images based on it by systematically changing orientation of the local viewing direction vectors D of points P discussed above. Overall, it is clear that the scope of the invention in view of displaying the imaged anatomy based on a frame data acquired in a single panoramic imaging scan includes any combination of modifying the virtual panorama curve 400 and orientation of the local direction vectors D of points P, including modifying only a selected number of the vectors D, so as to display different layers of the anatomy and from different angles of view, or only either of these.

The embodiments discussed here make it possible to use for dental frame panoramic imaging a dental panoramic imaging apparatus which includes an x-ray source having a focus and an image detector having a number of pixel columns, the x-ray source and the image detector being arranged to the apparatus at a first distance from each other, a drive means for moving the x-ray source and the detector around a patient's head, a control system including means to control the apparatus to take several individual overlapping frames along a dental arch, in which the detector is implemented as wide or wider than a second distance and the control system is arranged to control the apparatus to take frames whose width is equal to the second distance, the second distance being of about 2-10% of said first distance.

Here, the distance between the x-ray source and the image detector may preferably be about 500-550 mm.

A further advantage is that in cases, one will be able to display anatomies which otherwise could not be made visible, not at least without exposing the patient to a further panoramic irradiation process. When one is able to change the angle of view, details of the imaged anatomy may become visible which otherwise would not be visible. For example, a tooth filling may hamper getting a tooth on the other side of the dental arch visible, but changing the viewing direction may be able to bring such tooth visible after all.

Figure 7:
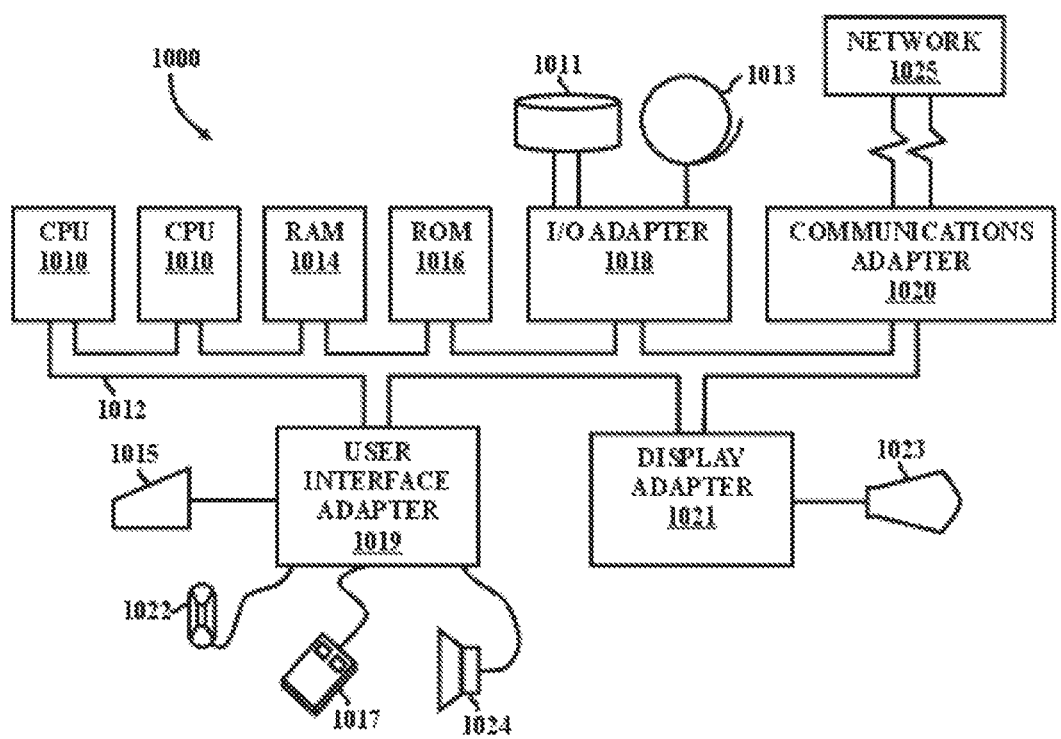

Shown in FIG. 7 is a schematic drawing which illustrates a hardware configuration of an information handling/computer system by which embodiments of the invention may be realized. System 1000 of FIG. 7 comprises at least one processor or central processing unit (CPU) 1010. The CPUs 1010 are interconnected via system bus 1012 to various devices such as a random access memory (RAM) 1014, read-only memory (ROM) 1016, and an input/output (I/O) adapter 1018. The I/O adapter 1018 can connect to peripheral devices, such as disk units 1011 and tape drives 1013, or other program storage devices that are readable by system 1000. System 1000 can read the inventive instructions on the program storage devices and follow these instructions to execute the methodology of the embodiments herein. The system further includes a user interface adapter 1019 that connects a keyboard 1015, mouse 1017, speaker 1024, microphone 1022, and/or other user interface devices such as a touch screen device (not shown) to the bus 1012 to gather user input. Additionally, a communication adapter 1020 connects the bus 1012 to a data processing network 1025, and a display adapter 1021 connects the bus 1012 to a display device 1023 which may be embodied as an output device such as a monitor, printer, or transmitter, for example.

Thus, a further embodiment includes a dental panoramic imaging apparatus which includes an x-ray source having a focus and an image detector having a number of pixel columns, the x-ray source and said image detector being arranged to the apparatus at a distance from each other, a drive means for moving the x-ray source and the detector around a patient's head, a control system including means to control the apparatus to take several individual overlapping frames along a dental arch, and a user interface to send control commands to said control system, the control system including recorded information on location and orientation of the x-ray source and the x-ray detector at times when taking the frames, and a means for calculating a panoramic image by summing information of the frames with respect to said information so as to generate panoramic images as viewed from at least two different directions, the user interface including a means to give at least one control command relating to showing the at least two panoramic images as viewed from the at least two different directions.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the appended claims.

The invention claimed is:

1. A method for generating a digital dental panoramic image, comprising:
   using several individual overlapping frames (300) taken along a dental arch by a dental panoramic x-ray imaging apparatus, said apparatus including:
      an x-ray source for generating an x-ray beam and having a focus, and
      an image detector having pixel columns and said frames (300) being taken by moving the x-ray source and the image detector around a patient's head, and calculating the panoramic image (200) by summing information of the frames (300), wherein
the panoramic image (200) is generated by summing information of the frames (300) with respect to information of location and orientation of the x-ray beam and the x-ray detector at times when taking the frames,
a virtual panorama curve (400) with respect to said information of location and orientation of the x-ray beam and the x-ray detector is generated which represents a desired tomographic layer to be shown by the panoramic image(200),
for a column C of the panoramic image (200) being generated, a desired point P on said curve (400) is determined, and
a column C of the panoramic image (200) is generated by summing those columns of the individual frames (300) to which the point P as viewed from the focus of the X-ray source is projected, this projection P~P' defining a projection direction of the point P concerning the particular individual frame (300).

2. The method according to claim 1, wherein location of the desired point or points P with respect to said information of location and orientation of the x-ray beam and the x-ray detector at times when taking the frames is determined and said summing of information of the frames (200) includes summing a column or columns C of the panoramic image (200) with respect to said point or points P.

3. The method according to claim 1, wherein the virtual panorama curve (400) and said information of location and orientation of the x-ray beam and the x-ray detector are placed in the same set of coordinates, and
the panoramic image (200) is generated which represents a tomographic layer according to location of said curve (400) in said set of coordinates.

4. The method according to claim 2, wherein
a desired viewing direction D is determined for at least one point P and a weighting factor is calculated for a column on an individual frame (300) as based on an angle between the viewing direction D and a direction defined by a line from the focus of the radiation source to said point P, and
said weighting factor is used when summing said information of the frames (300) so as to give the less weight to a column of a frame the greater the angle between said directional vector D representing the desired viewing direction and said direction defined by a line from the focus of the radiation source to said point P.

5. The method according to claim 1, wherein pixel values of the columns C of panoramic image (200) are normalized by dividing pixel values of a given column C by the total sum of weighting factors of that column.

6. A method for generating and presenting digital dental panoramic images, comprising:
using several individual overlapping frames (300) taken along a dental arch by a dental panoramic x-ray imaging apparatus, said apparatus including:
an x-ray source for generating an x-ray beam and having a focus,
an image detector having pixel columns and
a display in functional connection with said apparatus and said frames (300) being taken by moving the x-ray source and the image detector around a patient's head,
calculating the panoramic image (200) by summing information of the frames (300), and
presenting the panoramic image (200) of a tomographic layer thus generated on the display, wherein at least two panoramic images (200) as viewed from different directions are generated and
said at least two images representing views from different directions are presented on the display simultaneously, in succession, as a combination image or as a moving image.

7. The method according to claim 6, wherein said generating of at least two panoramic images (200) includes summing information of said frames (300) by at least two different ways with respect to information of location and orientation of the x-ray beam and the x-ray detector at times when taking the frames.

8. The method according to claim 6, wherein the at least two panoramic images (200) are presented on the display in succession according to the order of their viewing direction so as to give an impression of the dental arch turning on the display.

9. The method according to claim 8, wherein
several panoramic images (200) as viewed from different directions are generated,
for each such viewing direction, several images representing different tomographic layers are generated,
for each such viewing direction, one of said several images representing different tomographic layers is selected to represent said viewing direction, and
the images thus selected are presented on the display.

10. The method according to claim 7, wherein location of a desired point or points P with respect to said information of location and orientation of the x-ray beam and the x-ray detector at times when taking the frames is determined and said summing of information of the frames (200) includes summing a column or columns C of the panoramic image (200) with respect to said point or points P.

11. The method according to claim 6, wherein
a virtual panorama curve (400) is generated which represents a tomographic layer to be shown in the panoramic image (200), and this curve (400) and said information of location and orientation of the x-ray beam and the x-ray detector are placed in the same set of coordinates, and
said at least two panoramic images (200) as viewed from different directions are generated by summing said information of the frames (300) with respect to said curve (400) so that the curve (400) is arranged in at least a first and a second orientation in said set of coordinates so that concerning each of the orientations,
for a column C of the panoramic image (200) being generated, a point P on said curve (400) is determined, and
a column C of the panoramic image (200) is generated by summing those columns of the individual frames (300) to which the point P as viewed from the focus of the radiation source is projected, this projection P~P' defining a projection direction of the point P concerning the particular individual frame (300).

12. A dental panoramic imaging apparatus, including:
an x-ray source (26) having a focus and an image detector (16) having a number of pixel columns,
said x-ray source (26) and said image detector(16) being arranged to the apparatus at a distance from each other,
a drive means (1) for moving the x-ray source (26) and the detector (16) around a patient's head,
a control system CS including means to control the apparatus to take several individual overlapping frames (300) along a dental arch, and
a user interface UI to send control commands to said control system, wherein the control system CS includes information of location and orientation of the x-ray source (26) and the x-ray detector (16 at times when taking the frames (300) and a means IP to calculate panoramic images (200) by summing information of the frames (300) with respect to said location and orientation information so as to generate panoramic images (200) as viewed from at least two different directions, and wherein the user interface UI includes a means to give at least one control command relating to showing the at least two panoramic images (200) as viewed from said at least two different directions.

13. The apparatus according to claim 12, wherein said control system CS includes a means to show said at least two images (200) representing views from different directions simultaneously, in succession, as a combination image or as a moving image.

14. The apparatus according to claim 12, wherein said control system CS includes means to present said images (200) in succession according to the order of their viewing direction so as to give an impression of a turning dental arch.

15. The apparatus according to claim 12, wherein said control system CS includes means IP to generate said at least two panoramic images (200) by summing information of the frames (300) by at least two different ways with respect to information of location and orientation of the x-ray source (26) and the x-ray detector (16) at times when taking the frames (300).

16. The apparatus according to claim 12, wherein said means IP to calculate panoramic images (200) include a means to sum information of the frames (300) with respect to information of location and orientation of the x-ray beam and the x-ray detector at times when taking the frames.

17. The apparatus according to claim 16, wherein said means IP to calculate panoramic images (200)include a means to generate a virtual panorama curve (400) which represents a tomographic layer to be shown by the panoramic image (200) and place this curve (400) and said information of location and orientation of the x-ray beam and the x-ray detector in the same set of coordinates, and to generate the panoramic image (200) which represents a tomographic layer according to location of said curve (400) in said set of coordinates.

18. The apparatus according to claim 16, wherein said means IP to calculate include a means to generate a virtual panorama curve (400) with respect to said information of location and orientation of the x-ray beam and the x-ray detector which represents a desired tomographic layer to be shown by the panoramic image (200) and, to determine for a column C of the panoramic image (200) being generated a desired point P on said curve (400), and to generate a column C of the panoramic image (200) by summing those columns of the individual frames (300) to which the point P as viewed from the focus of the radiation source is projected, this projection P~P' defining a projection direction of the point P concerning the particular individual frame (300).

19. A dental panoramic imaging apparatus, including:
an x-ray source (26) having a focus and an image detector (16) having a number of pixel columns,
said x-ray source (26) and said image detector (16) being arranged to the apparatus at a first distance from each other,
a drive means (1) for moving the x-ray source (26) and the detector (16) around a patient's head,
a control system CS including means to control the apparatus to take several individual overlapping frames (300) along a dental arch, wherein
the control system CS includes information of location and orientation of the x-ray source (26) and the x-ray detector (16) at times when taking the frames (300) and a means IP to calculate panoramic images (200) by summing information of the frames (300) with respect to said location and orientation information,
said detector (16) is implemented as wide or wider than a second distance and
the control system is arranged to control the imaging apparatus to take frames (300) whose width is equal to the second distance, the second distance being of about 2-10% of said first distance.

20. The apparatus according to claim 19, wherein said first distance is about 500-550 mm.

21. The apparatus according to claim 19, wherein said means IP to calculate panoramic images (200) include a means to generate a virtual panorama curve (400) which represents a tomographic layer to be shown by the panoramic image (200) and place this curve (400) and said information of location and orientation of the x-ray beam and the x-ray detector in the same set of coordinates, and to generate the panoramic image (200) which represents a tomographic layer according to location of said curve (400) in said set of coordinates.

22. The apparatus according to claim 21, wherein said means IP to calculate include a means to generate a virtual panorama curve (400) with respect to said information of location and orientation of the x-ray beam and the x-ray detector which represents a desired tomographic layer to be shown by the panoramic image (200) and, to determine for a column C of the panoramic image (200) being generated a desired point P on said curve (400), and to generate a column C of the panoramic image (200) by summing those columns of the individual frames (300) to which the point P as viewed from the focus of the radiation source is projected, this projection P~P' defining a projection direction of the point P concerning the particular individual frame (300).

\* \* \* \* \*